United States Patent [19]

Bahrmann et al.

[11] Patent Number: 4,578,523

[45] Date of Patent: Mar. 25, 1986

[54] PROCESS FOR THE PREPARATION OF ALDEHYDES

[75] Inventors: Helmut Bahrmann, Hamminkeln; Boy Cornils, Dinslaken; Werner Konkol; Wolfgang Lipps, both of Oberhausen, all of Fed. Rep. of Germany

[73] Assignee: Ruhrchemie Aktiengesellschaft, Oberhausen, Fed. Rep. of Germany

[21] Appl. No.: 738,822

[22] Filed: May 29, 1985

[51] Int. Cl.$^4$ .............................................. C07C 45/50
[52] U.S. Cl. .................................. 568/454; 502/164; 502/166; 568/455; 556/136
[58] Field of Search ............... 260/429 R; 502/164, 502/166; 568/454, 455

[56] References Cited

U.S. PATENT DOCUMENTS

| Re. 31,812 | 1/1985 | Kuntz | 568/454 |
| 4,390,729 | 6/1983 | Oswald | 568/454 |

FOREIGN PATENT DOCUMENTS

| 0007609 | 2/1980 | European Pat. Off. | 568/454 |
| 3301591 | 7/1984 | Fed. Rep. of Germany | 568/454 |
| 2478078 | 9/1981 | France | 568/454 |
| 0216138 | 12/1983 | Japan | 568/454 |

Primary Examiner—Werren B. Lone
Attorney, Agent, or Firm—Jordan B. Bierman

[57] ABSTRACT

A novel process for the preparation of aldehydes by reacting olefins with carbon monoxide and hydrogen in the presence of a catalyst system comprised of rhodium in metallic form or as a compound and a water-soluble quaternary ammonium salt of a mono, di or trisulfonated arylphosphine.

5 Claims, No Drawings

PROCESS FOR THE PREPARATION OF ALDEHYDES

STATE OF THE ART

It is known that aldehydes and alcohols can be prepared by the reaction of olefins with carbon monoxide and hydrogen which reaction is catalyzed by hydridometal carbonyls, preferably those of the metals of the 8th group of the Periodic Table. Apart from cobalt which is widely used in industry as a catalyst metal, rhodium has also been gaining in importance recently. In contrast to cobalt, rhodium makes it possible for the reaction to be carried out at low pressure and furthermore, the reaction takes place with enhanced formation of straight-chained n-aldehydes with iso-aldehydes only being formed to a minor degree. Finally, the hydrogenation of olefins to saturated hydrocarbons is also appreciably lower with rhodium catalysts than with cobalt catalysts.

In the commercial processes, the rhodium catalyst is in the form of a modified hydridorhodium carbonyl containing additional ligands, if necessary in excess. Tertiary phosphines or phosphites have proved to be particularly good as ligands and by using them, it is possible to reduce the reaction pressure to values under 300 bar ($3 \times 10^4$ kPa). However, the separation of the reaction products and the recovery of the catalyst dissolved homogeneously in the reaction product present problems in this process. Generally, the reaction product is distilled out of the reaction mixture, but this method can only be used in practice for the hydroformylation of low molecular weight olefins, i.e. olefins with up to about 5 carbon atoms in the molecule due to the thermal sensitivity of the aldehydes and alcohols formed. Furthermore, it has been shown that the thermal loading of the distillation product also leads to considerable catalyst losses due to decomposition of the rhodium complex compounds.

The said shortcomings are avoided by the use of catalyst systems which are soluble in water and such catalysts are, for example, described in the DE No. 26 27 354. Solubility of the rhodium complex compounds is achieved by the use of sulfonated triarylphosphines as complex components. In this version of the process, the catalyst is separated from the reaction product after completion of the hydroformylation reaction simply by separation of the aqueous and organic phases, i.e. without distillation and thus without additional thermal process steps. A further characteristic of this method is that n-aldehydes are formed with a high selectivity from terminally unsaturated olefins and iso-aldehyes are formed only to a minor degree. Apart from sulfonated triarylphosphines, carboxylated triarylphosphines are also used as complex components of water-soluble rhodium complex compounds.

The known processes have proved to be admirably suitable for the hydroformylation of lower olefins, in particular ethylene and propylene. However, if higher olefins such as hexene, octene or decene are used, the conversion and/or the selectivity towards n-compounds drop(s) appreciably. Thus, the reaction is often no longer economical on a commercial scale. The drop in yield is caused by the fact that higher olefins are less soluble in water since the reaction between the two reactants takes place in the aqueous phase.

Admittedly, DE No. 31 35 127 does teach hydroformylation of olefinic compounds in a system containing an aqueouse phase and an organic phase, which is either immiscible or only slightly miscible with it in the presence of solubilizers. The practical performance of this reaction is limited exclusively to the use of monosulfonated or monocarboxylated triarylphosphines as a component of the rhodium complex compound. It has been shown that the monosulfonated triphenylhphosphine in particular leads only to a moderate conversion and that the selectivity towards straight-chained n-aldehydes is low.

Conversion and selectivity can be improved by using trisulfonated triarylphosphines instead of monosulfonated compounds. However, an unsatisfactory aspect of this process variant is that rhodium and water-soluble phosphine are removed with the organic reaction product—even if only in small amounts—so that in many cases an additional working-up step is necessary. A further disadvantage is the related lowering of the normal-iso ratio.

OBJECTS OF THE INVENTION

It is an object of the invention to overcome the disadvantages of the prior art and develope a procedure which also permits the hydroformylation of higher olefins in a multi-phase system consisting of aqueous catalyst solution and organic starting materials and in some cases reaction products as well as gaseous reactants.

This and other objects and advantages of the invention will become obvious from the following detailed description.

THE INVENTION

In the novel process of the invention for preparation of aldehydes by reacting olefins with carbon monoxide and hydrogen in the liquid phase in the presence of water and rhodium in metallic form or as a compound as well as a water-soluble arylphosphine at temperatures of 20° to 150° C. and 1 to 200 bar (100 to $2 \times 10^4$ kPa), the improvement comprises that the water-soluble phosphine has the formula

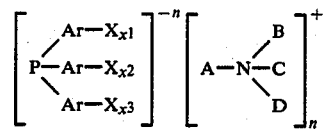

where Ar is aryl and X is a sulfonic acid, $x^1$, $x^2$ and $x^3$ are 0 or 1 with the proviso that at least one of $x^1$, $x^2$ or $x^3$ is 1, A is selected from the group consisting of an alkyl of 1 to 18 carbon atoms and aralkyl of 7 to 18 carbon atoms and B,C,D are alkyl of 1 to 4 carbon atoms and n is a whole number between 1 and 3.

Surprisingly, it has been proven that when water-soluble phosphines are used in the process of the invention the high activity and selectivity of the catalyst system is maintained even when high olefins are hydroformylated. At the same time, however, the amount of phosphine removed with the organic reaction product is also reduced considerably.

The water-soluble phosphines used in the new process obviously improve the solubility of the organic substrate in the aqueous phase and thus contribute towards an increase in the conversion. Their extremely low solubility in the organic phase means that they themselves and the metallic components of the catalyst system are either not removed with the reaction product from the reaction zone, or if so, only a negligibly small amount. Thus there is no need for a separate working-up step for the recovery of rhodium from the aldehyde.

Of the water-soluble phosphines of the above formula, preferred compounds are those wherein Ar is phenyl or naphthyl, the sum of $x^1$, $X^2$ and $x^3$ is 2 or 3 and B,C and D are the same alkyl of 1 to 4 carbon atoms. Examples of water-soluble phosphines suitable for carrying out the new process are triphenyl trisulfonates and triphenyldisulfonates with the following cations: trimethylcetylammonium, trimethyldodecylammonium, tributyldodecylammonium, dodecylethyldimethylammonium, trithylbenzylammonium.

The phosphines used in the claimed process are prepared by treating sulfonated triarylphosphines with oleum and it is possible to prepare mono, di or trisulfonated arylphosphines by variation of the reaction conditions, particularly the reaction time, reaction temperature and the ratio of triarylphosphine to sulfuric trioxide.

It is practical to first recover amine salts from the sulfonation product which are insoluble in water but soluble in organic solvents. They are then converted to the desired "onium" salt of the triarylphosphine by treatment with a quaternary ammonium hydroxide.

The reaction of the olefin with hydrogen and carbon monoxide by the process of the invention takes place at temperature of 20° to 150° C., particularly 50° to 120° C. and pressures of 1 to 200 bar (100 to $2 \times 10^4$ kPa), particularly 10 to 100 bar ($1 \times 10^3$ to $1 \times 10^4$ kPa).

The catalyst can be added to the reaction system in a preformed state but it can also be successfully prepared in the reaction mixture from the components rhodium or a rhodium compound and the aqueous solution of the quaternary ammonium salt of the sulfonated triarylphosphine under reaction conditions, i.e. in the presence of the olefin. In addition to metallic rhodium in finely distributed form, water-soluble rhodium salts such as rhodium chloride, rhodium sulfate, rhodium acetate or compounds soluble in organic media such as rhodium-2-ethylhexanoate or insoluble compounds such as rhodium oxides can be used as sources of rhodium.

The rhodium concentration in the aqueous catalyst solution is 10 to 2000 ppm by weight based on the solution. The quaternary ammonium salt of the sulfonated phosphine is added in such an amount that for 1 g atom of rhodium, 1 to 300 mol, preferably 2 to 100 mol, of phosphine compound are present. The pH value of the aqueous catalyst solution should not be below 2 and generally, a pH value of 2 to 13, preferably 4 to 10 is established.

The composition of the synthesis gas, i.e. the ratio of CO to hydrogen can be varied within wide limits. Generally, a synthesis gas is used where the volume ratio of CO to hydrogen is 1:1 or only deviates slightly from this value. The reaction can be carried out both as a batch process and continuously. The process of the invention is successfully used for hydroformylation of strightchained or branched olefins of four or more and in particular with six to twenty carbon atoms. The double bond in these atoms can be terminal or internal.

The following examples serve to illustrate the invention more closely without limiting it to the embodiments described therein. To characterize the efficiency of the catalyst systems, apart from the ratio of n-aldehyde to i-aldehyde, the term "activity" is defined as $$\frac{\text{mol aldehyde}}{\text{g-atom Rh} \times \text{min}}$$

The formation of alcohols and hydrocarbons is minimal.

EXAMPLE 1 (Comparison)

420 g (corresponding to 355 ml) of an aqueous solution containing 15.5% by weight of the sodium salt of tri(m-sulfophenyl) phosphine and 400 ppm of rhodium in the form of rhodium acetate were placed in a 1 liter autoclave with a dip-pipe and then, synthesis gas ($CO/H_2 = 1:1$) was forced in up to a pressure of 25 bar. The reaction solution was treated with the synthesis gas for 3 hours at 125° C. accompanied by stirring and it was then cooled to about 30° C. The stirring was stopped and after a settling period of 15 minutes, the excess solution ($\approx 61$ g) was forced out through the dip-pipe and analyzed and the residual solution remained in the autoclave. After the resumption of stirring, 170 g of n-hexene-1 were pumped through a pressure pipe into the autoclave and while the pressure was maintained at 25 bar, the mixture was heated to 125° C. over a period of 3 hours. It was then allowed to cool to 30° C. and settle. After a 15 minute settling period, the uppermost organic phase was forced out through the dip-pipe and was weighed and subjected to a gas chromatographic analysis.

Hydroformylation was repeated a total of 6 times whereby more or less the same results were achieved. The activity values listed in Table I relate to the amounts of aqueous and organic phases present in the autoclave after each run.

TABLE I

| No. of hydroformylations | 1 | 2 | 3 | 4 | 5 | 6 | 7 |
|---|---|---|---|---|---|---|---|
| Conversions (% to GC) | 21 | 18 | 21 | 21 | 20 | 21 | 19 |
| n/i ratio | 98/2 | 98/2 | 98/2 | 98/2 | 98/2 | 98/2 | 98/2 |
| aqueous phase in the reactor (g) | 359 | 359 | 359 | 357 | 357 | 357 | 356 |
| organic phase from the reactor (g) | 175 | 174 | 176 | 175 | 175 | 165 | 175 |
| activity $\frac{\text{mol C}_7\text{-aldehyde}}{\text{g-atom Rh} \times \text{min}}$ | 1.28 | 1.09 | 1.29 | 1.29 | 1.23 | 1.21 | 1.17 |

To determine the total amount of rhodium and phosphorus removed with the organic phase, the organic components drawn off from the reactor in the individual tests were combined, concentrated to about 1/10th of their original volume and analyzed. 0.017 ppm by weight of rhodium and 0.34 ppm by weight of phosphorus (in each case based on the original organic phase) were found.

EXAMPLE 2

Example 1 was repeated with the exception that 315 g (corresponding to 295 ml) of an aqueous solution of the trimethylbenzylammonium salt of tri-(m-sulfophenyl)phosphine with a P(III) content of 0.308% by weight and 158 g of n-hexene-1 were used in the hydroformylation process instead of the sodium salt. The test results are reported in Table 2. The rhodium and phosphorus losses were determined by the method described in Example 1. An average of 0.029 ppm by weight of rhodium and 0.98 ppm by weight of phosphorus were removed with the organic product, i.e. only slightly more than when the normally employed sodium salt of tri-(m-sulfophenyl)phosphine was used.

TABLE 2

| | EXAMPLE 2 | | | | | | | |
|---|---|---|---|---|---|---|---|---|
| No. of hydroformylations | 1 | 2 | 3 | 4 | 5 | 6 | 7 | 8 |
| conversion (% to GC) | 48 | 55 | 51 | 50 | 41 | 38 | 41 | 41 |
| n/i ratio | 93/7 | 93/7 | 93/7 | 94/6 | 94/6 | 94/6 | 94/6 | 94/6 |
| aqueous phase in the reactor (g) | 315 | 314 | 312 | 312 | 311 | 309 | 309 | 308 |
| organic phase from the reactor (g) | 180 | 198 | 182 | 155 | 164 | 160 | 158 | 178 |
| activity $\frac{\text{mol } C_7 \text{ aldehydes}}{\text{g atom Rh} \times \text{min}}$ | 3.43 | 4.34 | 3.72 | 3.11 | 2.71 | 2.46 | 2.62 | 2.96 |

EXAMPLES 3 TO 5

Examples 3 to 5 were carried out by the method described in Example 1 with the exception that instead of the sodium salt of tri-(m-sulfophenyl)phosphine; 420 g (corresponding to 390 ml) of an aqueous solution containing 46% by weight of the dodecylethyldimethylammonium salt of tri-(m-sulfphenyl)phosphine (Example 3); 820 g (corresponding to 740 ml) of an aqueous solution containing 25% by weight of the benzyltrimethylammonium salt of di-(m-sulfophenyl)-phenylphosphine (Example 4); 420 g (corresponding to 390 ml) of an aqueous solution containing 23% by weight of the benzyltriethylammonium salt of tri-(m-sulfophenyl)-phosphine (Example 5) were used. The test results are reported in Table 3.

TABLE 3

| | Examples | | |
|---|---|---|---|
| TPPTS onium salt | 3 | 4 | 5 |
| olefin | 1-hexene | 1-hexene | 1-hexene |
| φ conversion (% to GC) | 97 | 78 | 60 |
| φ n/i ratio | 77/23 | 96/4 | 96/4 |
| φ activity $\frac{\text{mol aldehyde}}{\text{g atom Rh} \times \text{min}}$ | 13.3 | 5.4 | 5.0 |
| No. of hydroformylations with the same catalyst solution | 15 | 10 | 10 |

3 dodecylethyldimethylammonium/TPPTS (420 g = 390 ml of a 46% solution)
4 benzyltrimethylammonium/TPPDS (820 g = 740 ml of a 27% solution)
5 benzyltriethylammonium/TPPTS (410 g = 390 ml of a 23% solution)

EXAMPLES 6 AND 7

Examples 6 and 7 were also carried out under the conditions of Example 1 but with styrene as the olefin. In Example 6 (comparison), the Na-salt (420 g corresponding to 375 ml of a 22% by weight-solution) and in Example 7, the dodecylethyldimethylammoniun salt (420 g corresponding to 391 ml of a 23% by weight solution) of tri-(m-sulfophenyl)-phosphine were used. The results of the tests are reported in Table 4 and as can be clearly seen, the quaternary ammonium salt favored the formation of α-phenylpropionaldehyde.

TABLE 4

| | Examples | |
|---|---|---|
| TPPTS onium salt | 6 | 7 |
| olefin | styrene | styrene |
| φ conversion (% to GC) | 6 | 100 |
| φ β/α ratio | 40/60 | 26/74 |
| φ activity $\frac{\text{mol aldehyde}}{\text{g atom Rh} \times \text{min}}$ | 0.2 | 6.5 |
| No. of hydroformylations with the same catalyst solution | 5 | 5 |

6 TPPTS Na salt (comparison) (420 g = 375 ml of a 22% solution)
7 dodecylethyldimethylammonium/TPPTS (420 g = 391 ml of a 23% solution)

Various modifications of the process of the invention may be made without departing from the spirit or scope thereof and it is to be understood that the invention is intended to be limited only as defined in the appended claims.

What we claim is:

1. In a process for the preparation of aldehydes by reacting olefins with carbon monoxide and hydrogen in the liquid phase in the presence of water and rhodium in metallic form or as a compound as well as a water-soluble arylphosphine at temperatures of 20° to 150° C. and 1 to 200 bar (100 to $2 \times 10^4$ kPa), the improvement comprising that the water-soluble phosphine has the formula

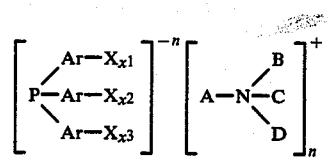

where Ar is aryl and X is a sulfonic acid $x^1$, $x^2$ and $x^3$ are 0 or 1 with the proviso that at least one of $x^1$, $x^2$ or $x^3$ is 1, A is selected from the group consisting of an alkyl of 1 to 18 carbon atoms and aralkyl of 7 to 18 carbon atoms and B,C,D are alkyl of 1 to 4 carbon atoms and n is a whole number between 1 and 3.

2. The process of claim 1 wherein Ar is phenyl or naphthyl.

3. The process of claim 1 wherein the sum of $x^1$, $x^2$ and $x^3$ is 2 or 3.

4. The process of claim 2 wherein the sum of $x^1$, $x^2$ and $x^3$ is 2 or 3.

5. The process of claim 1 wherein B,C and D denote the same alkyl.

* * * * *